US008639477B2

(12) United States Patent
Chelnokov et al.

(10) Patent No.: US 8,639,477 B2
(45) Date of Patent: Jan. 28, 2014

(54) RECONSTRUCTION OF NON-VISIBLE PART OF TOOTH

(75) Inventors: Fedor Chelnokov, Khimi Town (RU); Roman A. Roschin, Moscow (RU); Petr Ushanov, Khmiki (RU)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 13/362,997

(22) Filed: Jan. 31, 2012

(65) Prior Publication Data
US 2012/0203513 A1    Aug. 9, 2012

Related U.S. Application Data

(63) Continuation of application No. 12/055,192, filed on Mar. 25, 2008, now Pat. No. 8,108,189.

(51) Int. Cl.
| G06F 17/50 | (2006.01) |
| G06F 7/48 | (2006.01) |
| A61C 11/00 | (2006.01) |
| A61C 5/00 | (2006.01) |
| A61C 3/00 | (2006.01) |

(52) U.S. Cl.
USPC ................... 703/1; 703/7; 433/213; 433/223; 433/24

(58) Field of Classification Search
USPC ................ 703/7, 1, 2; 433/24, 6, 213, 215, 2; 345/418–420; 700/98
See application file for complete search history.

(56) References Cited

U.S. PATENT DOCUMENTS

| 5,121,333 A | 6/1992 | Riley et al. |
| 5,257,203 A | 10/1993 | Riley et al. |
| 5,549,476 A | 8/1996 | Stern |
| 5,886,702 A | 3/1999 | Migdal et al. |
| 5,975,893 A | 11/1999 | Chishti et al. |
| 6,227,850 B1 | 5/2001 | Chishti et al. |
| 6,386,878 B1 | 5/2002 | Pavlovskaia et al. |
| 6,409,504 B1 | 6/2002 | Jones et al. |

(Continued)

FOREIGN PATENT DOCUMENTS

JP    9019443    7/1995

OTHER PUBLICATIONS

Pose estimation of teeth through crown-shape matching Vevin W.Y. Mok et al; Medical Imaging 2002: Image Processing, Milan Sonka, J. Michael Fitzpatrick, Editors, Proceedings of SPIE vol. 4684 (2002) © 2002 SPIE; pp. 955-964.*

*Primary Examiner* — Akash Saxena
(74) *Attorney, Agent, or Firm* — Brooks, Cameron & Huebsch, PLLC

(57) ABSTRACT

A computer-implemented method for modeling a complete tooth of a patient to facilitate dental and/or orthodontic treatment. The method includes generating a first set of digital data representing a clinical crown; generating a second set of digital data representing a plurality of digital tooth models of a particular tooth type each having a first parameterization; processing the second set of digital data to obtain a third set of digital data representing an average tooth model of the particular tooth type having a second parameterization which is less than the first parameterization; fitting the third set of digital data to the first set of digital data to create a set of digital data representing an interim tooth model; and morphing the set of digital data representing the interim tooth model to substantially mimic the anatomical shape of the clinical crown of the first set of digital data.

20 Claims, 12 Drawing Sheets

(56) References Cited

U.S. PATENT DOCUMENTS

| | | | |
|---|---|---|---|
| 6,514,074 | B1 | 2/2003 | Chishti et al. |
| 6,621,491 | B1* | 9/2003 | Baumrind et al. ............ 345/419 |
| 6,685,469 | B2 | 2/2004 | Chishti et al. |
| 6,733,289 | B2 | 5/2004 | Manemann et al. |
| 7,040,896 | B2 | 5/2006 | Pavlovskaia et al. |
| 7,241,142 | B2 | 7/2007 | Abolfathi et al. |
| 7,329,122 | B1 | 2/2008 | Scott |
| 7,476,100 | B2 | 1/2009 | Kuo |
| 7,728,848 | B2 | 6/2010 | Petrov et al. |
| 7,806,687 | B2 | 10/2010 | Minagi et al. |
| 8,045,772 | B2* | 10/2011 | Kosuge et al. ............... 382/128 |
| 8,108,189 | B2* | 1/2012 | Chelnokov et al. ............... 703/7 |
| 2001/0002310 | A1* | 5/2001 | Chishti et al. .................... 433/24 |
| 2002/0037489 | A1* | 3/2002 | Jones et al. ..................... 433/24 |
| 2002/0064759 | A1 | 5/2002 | Durbin et al. |
| 2002/0177108 | A1* | 11/2002 | Pavlovskaia et al. ......... 433/215 |
| 2003/0027098 | A1* | 2/2003 | Manemann et al. ............ 433/24 |
| 2003/0068598 | A1 | 4/2003 | Vallittu et al. |
| 2004/0023188 | A1 | 2/2004 | Pavlovskaia et al. |
| 2004/0054304 | A1 | 3/2004 | Raby |
| 2004/0220691 | A1* | 11/2004 | Hofmeister et al. ............ 700/98 |
| 2005/0208449 | A1* | 9/2005 | Abolfathi et al. ............... 433/24 |
| 2006/0063135 | A1* | 3/2006 | Mehl ............................. 433/223 |
| 2006/0098007 | A1 | 5/2006 | Rouet et al. |
| 2006/0111631 | A1 | 5/2006 | Kelliher et al. |
| 2006/0147872 | A1 | 7/2006 | Andreiko |
| 2006/0275736 | A1 | 12/2006 | Wen et al. |
| 2006/0290693 | A1 | 12/2006 | Zhou et al. |
| 2007/0054231 | A1 | 3/2007 | Manemann et al. |
| 2008/0020350 | A1 | 1/2008 | Matov et al. |
| 2008/0057479 | A1 | 3/2008 | Grenness |
| 2008/0094389 | A1 | 4/2008 | Rouet et al. |
| 2009/0148809 | A1 | 6/2009 | Kuo et al. |
| 2009/0181346 | A1 | 7/2009 | Orth |
| 2009/0246726 | A1 | 10/2009 | Chelnokov et al. |
| 2010/0145664 | A1* | 6/2010 | Hultgren et al. .................... 703/1 |
| 2010/0216085 | A1* | 8/2010 | Kopelman ...................... 433/24 |
| 2010/0268515 | A1 | 10/2010 | Vogt et al. |
| 2011/0077913 | A1* | 3/2011 | Kuo et al. ......................... 703/1 |
| 2011/0104630 | A1* | 5/2011 | Matov et al. .................... 433/24 |
| 2012/0029883 | A1* | 2/2012 | Heinz et al. ...................... 703/1 |
| 2012/0040311 | A1* | 2/2012 | Nilsson ......................... 433/214 |
| 2012/0203513 | A1* | 8/2012 | Chelnokov et al. ............... 703/1 |

* cited by examiner

RECONSTRUCTION OF NON-VISIBLE PART OF TOOTH

CROSS-REFERENCE TO RELATED APPLICATIONS

This application is a continuation of U.S. patent application Ser. No. 12/055,192, filed Mar. 25, 2008, the entire contents of which are hereby incorporated by reference.

BACKGROUND

1. Field of the Invention

The present invention relates, generally, to dental and/or orthodontic treatment, and in particular to a system and method for modeling a complete tooth of a patient to facilitate dental and/or orthodontic treatment.

2. Related Art

Current techniques for impression-based computational orthodontics are based on impressions, three dimensional (3-D) radiographic scans or 3-D x-rays of teeth, which capture the surface of the teeth. Unfortunately, when two or more teeth are in close proximity, the digital data representing surfaces of the individual teeth are difficult to separate when using these techniques. The same problem exists for "unerupted" teeth, where the initial scan may capture only exposed portions of the teeth. The inability to account accurately for the interproximal and unerupted surfaces of the teeth means that aligners created based on the incomplete data may not properly fit in the areas that are later exposed either through eruption from the gingiva, uncrowding, or improved hygiene, which may firm up the gingival tissue and expose more tooth structure. An aligner that does not fit well becomes less effective in later stages of the orthodontic treatment. A poorly fitting aligner may also compromise the esthetics of the appliance, which in turn, may lead to suboptimal patient compliance in wearing the aligners.

SUMMARY

In accordance with various aspects of the present invention, a system and method are provided to account for the interproximal and unerupted surfaces of teeth ("invisible surfaces") that are partially blocked or unexposed in impressions, 3-D radiographic scans or 3-D X-rays to facilitate dental and/or orthodontic treatment.

Reconstruction of the invisible surfaces of the tooth surface is based on the visible or known surfaces. The reconstruction uses statistical preparation of a parametric tooth model, matching of the parametric model, and the final deformation step that guarantees the reconstructed model substantially follows the visible part and the transition area between known and reconstructed parts is anatomical.

In one aspect, a computer-implemented method is provided for modeling a complete tooth of a patient to facilitate dental and/or orthodontic treatment. The method includes generating a first set of digital data representing a clinical crown; generating a second set of digital data representing a plurality of digital tooth models of a particular tooth type each having a first parameterization; processing the second set of digital data to obtain a third set of digital data representing an average tooth model of the particular tooth type having a second parameterization which is less than the first parameterization; fitting the third set of digital data to the first set of digital data to create a set of digital data representing an interim tooth model; and morphing the set of digital data representing the interim tooth model to substantially mimic the anatomical shape of the clinical crown of the first set of digital data.

The suggested solution is stable with respect to minor impurities in the input data and sufficiently fast to be used in interactive mode.

This brief summary has been provided so that the nature of the invention may be understood quickly. A more complete understanding of the invention may be obtained by reference to the following detailed description in connection with the attached drawings.

BRIEF DESCRIPTION OF THE DRAWINGS

The foregoing features and other features of the present invention will now be described with reference to the drawings. In the drawings, the same components have the same reference numerals. The illustrated embodiment is intended to illustrate, but not to limit the invention. The drawings include the following Figures.

DETAILED DESCRIPTION

Figure 1A:
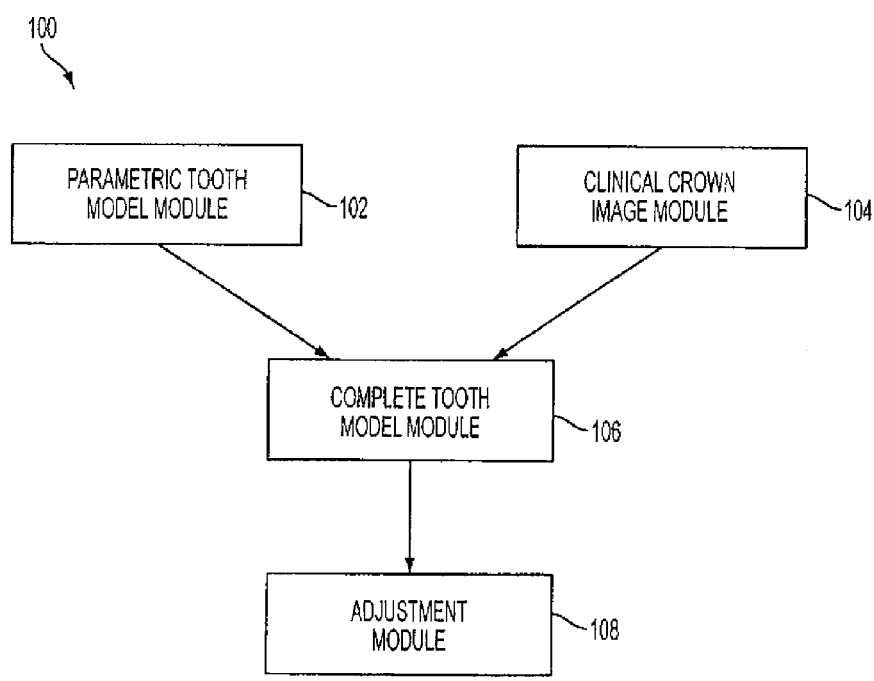
FIG. 1A is a flow diagram of a process for creating a complete tooth model from tooth images of teeth having partially blocked or unexposed surfaces in accordance with an embodiment of the present invention.

The present invention may be described herein in terms of various components and processing steps. It should be appreciated that such components and steps may be realized by any number of hardware and software components configured to perform the specified functions. For example, the present invention may employ various electronic control devices, visual display devices, input terminals and the like, which may carry out a variety of functions under the control of one or more control systems, microprocessors or other control devices.

In addition, the present invention may be practiced in any number of orthodontic or dental contexts and the exemplary embodiments relating to a system and method for modeling of complete tooth of a patient as described herein are merely a few of the exemplary applications for the invention. For example, the principles, features and methods discussed may be applied to any orthodontic or dental treatment application or process.

For illustrative purposes, the various exemplary methods and systems may be described in connection with a single tooth of a patient; however, such exemplary methods and systems may be implemented on more than one tooth and/or all teeth within a patient, such as molars, bicuspids, canines, incisors or any other teeth. For example, the exemplary methods and systems may be implemented by performing a particular process, operation or step on one or more teeth before proceeding to a subsequent process, operation or step, or by performing all or essentially all processes, operations or steps on a particular tooth before proceeding to another tooth, or any combination thereof.

Such modeling techniques may be conducted with one or more computer-based systems, such as systems configured for storing actual patient data and generic tooth data, morphing generic tooth data to such patient's data and/or facilitating additional orthodontic treatment applications, through the use of one or more algorithms.

The part of the tooth surface, which is visible in usual conditions, is called a "clinical crown" of the tooth. The present invention uses the known surfaces of the clinical crown to predict the unknown surfaces of the "invisible" or unseen part of the tooth.

In orthodontic applications, knowing the shape of the invisible parts of a tooth surface is important for esthetic reasons. For example, during the orthodontic treatment, the teeth are moving from their initial position to the final position. In final position, the initially invisible surfaces of the tooth may become visible. Thus, in order to predict the appearance of the whole jaw in the final position, the shape of the initially invisible surfaces is desired.

In addition, knowing the shape of the invisible parts of the tooth surface is important for tooth movements, since the interproximal surfaces of the tooth impose certain restrictions on tooth movements. These restrictions stem from the fact that the teeth are not allowed to "dive" into other teeth while moving from their initial to final position. To ensure that a treatment plan does not break these restrictions, the shape of the tooth in the interproximal areas should be known.

For makers of tooth related aligners and treatments, the shape of the invisible part of the tooth is of special interest, since in order to produce an appropriate aligner, the shape of the entire surface of a tooth during a given treatment stage should be known.

FIG. 1A illustrates a computer-implemented process 100 for modeling a complete tooth of a patient to facilitate dental and/or orthodontic treatment in a digital format from clinical crown images that are created from teeth having partially blocked or unexposed surfaces in accordance with the present invention.

In one embodiment, process 100 includes a parametric tooth model module 102 (hereinafter "module 102") for creating a digital data set representing a parametric tooth model 112 (FIG. 1B) from a set of etalon teeth. As defined herein, etalon teeth are reference teeth, manually prepared, or by other means, where all teeth of a particular type of tooth (e.g. incisor, canine) have substantially the same surface parameterization. Process 100 also includes clinical crown image module 104 (hereinafter "module 104") for creating a digital data set representing a surface image of a clinical crown 110 (FIG. 1B) of a patient with an incomplete surface portion. Incomplete tooth model module 106 (hereinafter "module 106") the parametric tooth model data set 112 generated in module 102 is fit to the patient's incomplete surface image data set 110 generated in module 104 to yield a complete tooth image data set 114.

In one embodiment, further adjustment of the complete tooth image may be provided through adjustment module 108. For example, the transition zone between the clinical crown and the generic tooth model may require "smoothing," as described in more detail below, so as to yield a tooth shape on complete tooth model which more closely approximates the clinical crown.

Figure 1C:
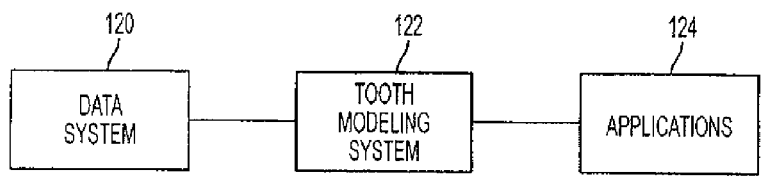
FIG. 1C illustrates a system for implementing the process of FIG. 1A in accordance with an embodiment of the present invention.
Figure 1B:
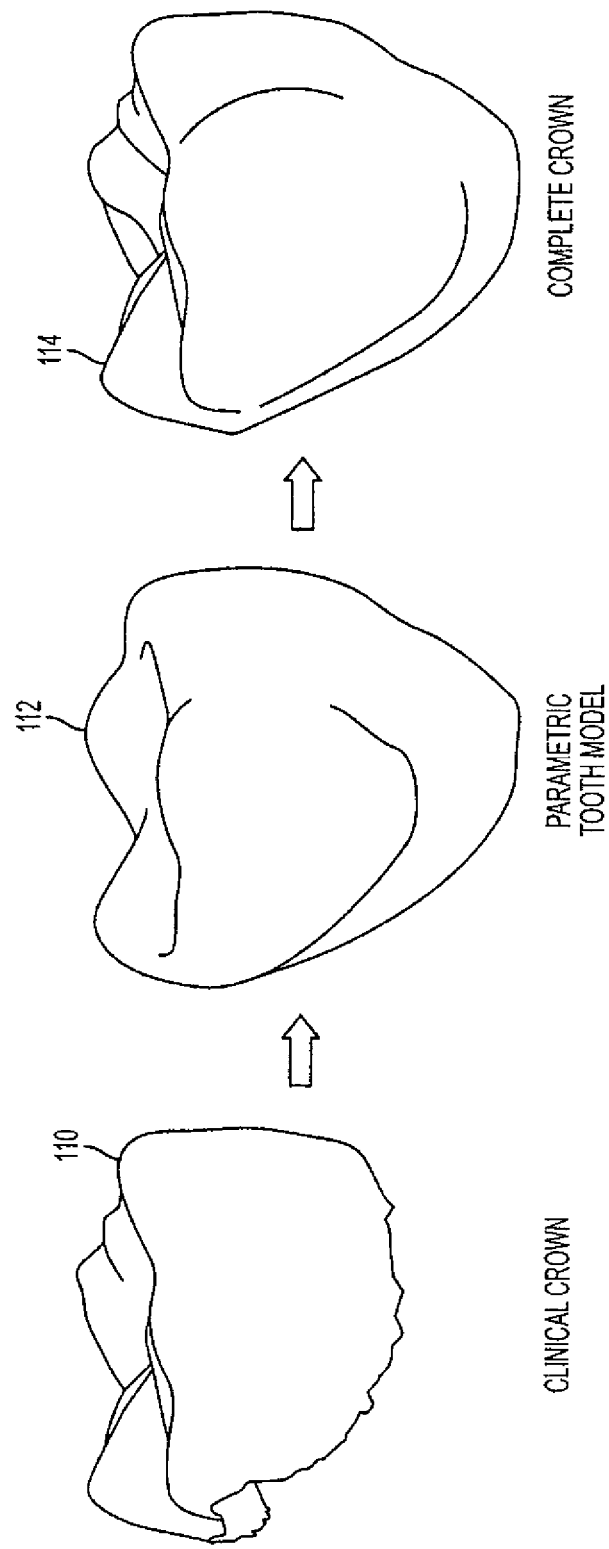
FIG. 1B illustrates graphically the implementation of the process of FIG. 1A in accordance with an embodiment of the present invention.

As shown in FIG. 1C, exemplary modeling methods of the present invention may be conducted with one or more computer-based systems, for example, a system 120 configured for storing patient data and generic tooth data. Also, a tooth modeling system 122 configured for executing module 102 and module 104 and for merging data and information generated from modules 102 and 104 to generate complete tooth model in module 106. A system 124 may be configured for facilitating any other conventional orthodontic treatment applications, such as methods or processes for tracking teeth movement and position, evaluating gingival effects, or any other orthodontic treatment process from pre-treatment to final stages, or any stages in between.

Systems 120, 122 and/or 124 may include one or more microprocessors, memory systems and/or input/output devices for processing modeling data and information. To facilitate modeling of a patient crown, tooth modeling system 120 may include one or more software algorithms configured for generating a complete tooth model and/or performing other functions set forth herein.

There are established techniques which may be used to obtain a 3D model of the clinical crown. Referring again to FIG. 1A, in module 104, data sets representing a patient's tooth crown may be generated by various techniques for creating a clinical crown image, such as those disclosed in U.S. Pat. No. 6,685,469, assigned to Align Technology, Inc. (the "'469 Patent"), herein incorporated by reference, in its entirety, for all purposes, or such modeling processes known and provided under the brands INVISALIGN® and CLINCHECK® that are available from Align Technology, Inc. of San Jose, Calif.

Figure 2:
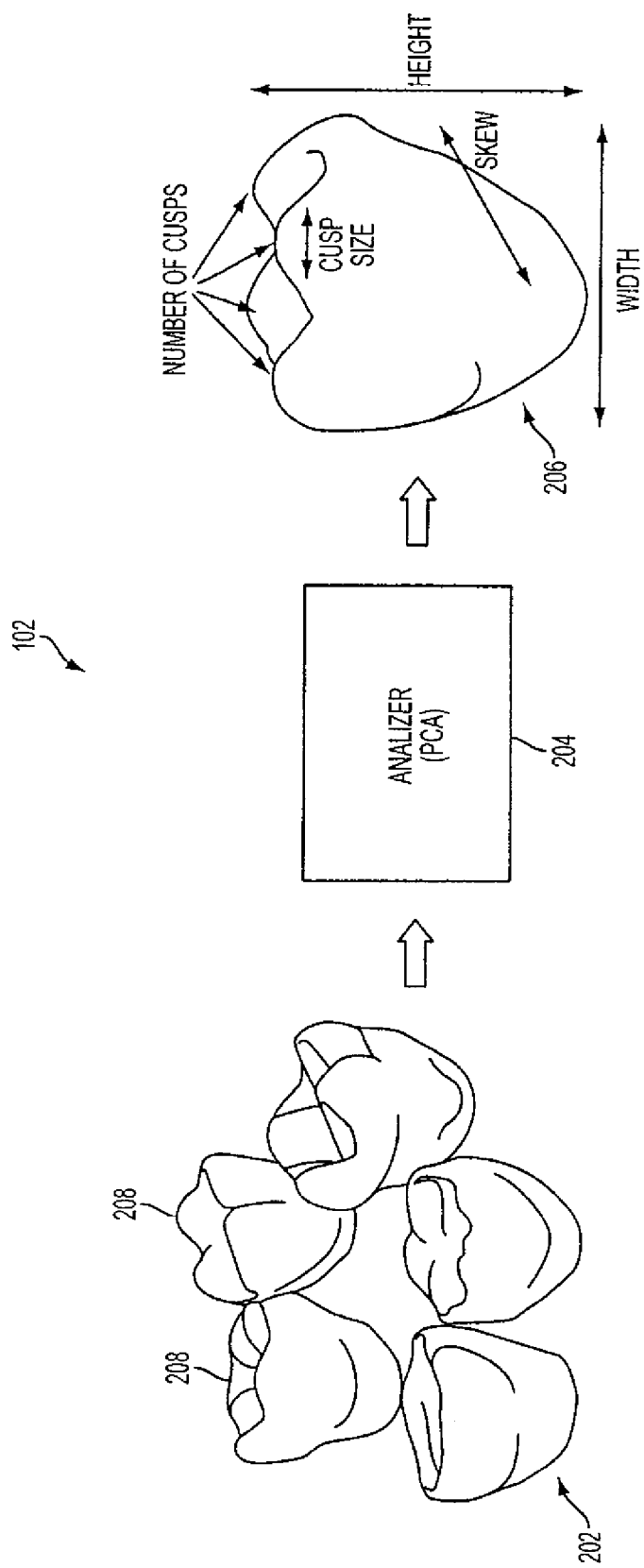
FIG. 2 is an illustration of the process of the parametric tooth model module in accordance with an embodiment of the present invention.

Referring to FIGS. 1A and 2, since human teeth show a high variety of shapes, module 102 provides a parametric model creation 206 which captures the high variety in a minimal number of numerical parameters. Thus, a large set of etalon teeth 202 is provided, which includes a large enough number of reconstructed teeth samples for representing as many tooth variations as possible. In module 102, a generic set of etalon teeth 202 are collected of each type of tooth. The set of etalon teeth 202 typically represents the same type of tooth (e.g. molar, canine, bicuspid, incisor and the like) as the clinical crown image it is intended to model, and may also be the same numbered tooth as the actual patient tooth, using conventional tooth numbering and identification systems.

The set of etalon teeth 202 may be scanned using well known destructive scanning techniques to provide the digital data representing the surface geometry of each tooth in the set.

The surface of each etalon tooth 208 may be represented by a triangular mesh, denoted as Mesh below. In one embodiment, the Mesh satisfies at least the following conditions: 1) topological equivalence to a sphere (Euler number=F−E+V=2, where F, E, V are the numbers of faces, edges and vertices in the Mesh, respectfully); and 2) no self-intersections. Thus, parametric tooth model 206 is a map:

$$M:(t, U, \alpha_i) \rightarrow \text{Mesh}$$

where t is a translation vector, U is a pure rotation, and $\alpha_i$, i=0, 1, . . . M are parameters describing the shape of parametric tooth model 206 (hereinafter "modes").

Once the surface representation is complete, parametric tooth model 206 may be obtained by analyzing the set of etalon teeth 202 provided using, for example, a Principal Components Analysis (PCA) technique 204 or a similar numeric technique. In one embodiment, the parameterization accomplished using PCA technique 204 allows description of any tooth with maximum accuracy using only a small number of parameters.

To begin PCA technique 204, the sample tooth set E is created which satisfies at least the following conditions: 1) all teeth shapes have the same number of vertices; and 2) corresponding shape vertices are located in similar positions.

The number of vertices in the Mesh is denoted as M. Each tooth shape may then be treated as a vector of length 3M:

$$e = \{x_1, y_1, z_1, x_2, y_2, z_2, \ldots, x_M, y_M, z_M\}.$$

Given N sample teeth and renumbering items of the sample tooth vector from 1 to 3M, all samples may be described as a matrix:

$$E = \begin{pmatrix} e_{11} & e_{12} & \cdots & e_{1N} \\ e_{21} & e_{22} & \cdots & e_{2N} \\ \vdots & \vdots & \ddots & \vdots \\ e_{3M1} & e_{3M2} & \cdots & e_{3MN} \end{pmatrix}.$$

The modes, described above, allow the model shape to be varied. The modes are equivalent to the eigenvectors of the covariance matrix of the sample tooth set E. The significance of the modes is determined by corresponding eigenvalues—the higher the eigenvalue, the greater the mode significance.

The mean shape of the shapes from E are found by:

$$\bar{e}_j = \frac{1}{N} \sum_{i=1}^{N} e_{ij}, j = 1, \ldots, 3M.$$

Next, the matrix X of deviations of samples $e_i$ from the mean $\bar{e}$:

$$X = \begin{pmatrix} e_{11} - \bar{e}_1 & e_{12} - \bar{e}_1 & \cdots & e_{1N} - \bar{e}_1 \\ e_{21} - \bar{e}_2 & e_{22} - \bar{e}_2 & \cdots & e_{2N} - \bar{e}_2 \\ \vdots & \vdots & \ddots & \vdots \\ e_{3M1} - \bar{e}_{3M} & e_{3M2} - \bar{e}_{3M} & \cdots & e_{3MN} - \bar{e}_{3M} \end{pmatrix}.$$

The covariance matrix C is:

$$C = \frac{1}{N-1} XX^T.$$

Next, the eigenvectors and corresponding eigenvalues of the covariance matrix C may be found. Since the size of covariance matrix C in this example, is 3M×3M and since 3M>>N, the evaluation of eigenvectors and eigenvalues can be very time and memory consuming. Thus, to reduce time and memory consumption, the eigenvectors and eigenvalues $\lambda_i$ of the matrix:

$$C' = \frac{1}{N-1} X^T X$$

may be solved, and the eigenvectors $v_i$ of covariance matrix C may be determined using the formula:

$$v_i = \frac{1}{\sqrt{\lambda_i}} X v'_i.$$

The variable v is an eigenvector of covariance matrix C:

$$Cv = \frac{1}{\sqrt{\lambda}} (XX^T)(Xv') = \frac{1}{\sqrt{\lambda}} X(X^T X) v' = \frac{1}{\sqrt{\lambda}} X C' v' = \sqrt{\lambda} X v' = \sqrt{\lambda} v.$$

Note that covariance matrix C has 3M eigenvalues and eigenvectors, while the Matrix C' has only N. The N eigenvalues (along with their eigenvectors) correspond to the N largest eigenvalues. All other eigenvalues of C are equal to 0. Orthogonal eigenvectors of C' are determined using standard mathematical algorithms. Eigenvectors of C formed using multiplication on X are also orthogonal as shown by:

$$v'^T_i v'_j = 0,$$

then $$v_i^T v_j = \frac{1}{\sqrt{\lambda_i \lambda_j}} v'^T_i (X^T X) v'_j = \sqrt{\frac{\lambda_j}{\lambda_i}} v'^T_i v'_j = 0.$$

It is clear that v has unit norm if v' has unit norm.

Now, given N eigenvectors, some may be selected as modes. The eigenvectors may be rearranged in order of decreasing eigenvalues and $g_i$ is computed:

$$g_i = \frac{\sum_{j=1}^{i} \lambda_j}{\sum_{k=1}^{N} \lambda_k} \times 100\%.$$

Then select first L, (1<L<N) eigenvectors so that the $g_L$ is above some threshold, for example, $g_L \geq 95\%$.

Although eigenvectors are orthogonal to each other, they are not orthogonal to the mean vector. Thus, it is possible for an eigenvector to have translation or rotation components, such that addition of the eigenvector to the mean is equivalent to some global translation or rotation of the mean shape.

Therefore, prior to filling matrix X for each sample tooth j, the best global scale $S_j$ and rigid transform $(U_j, t_j)$ is found for the mean that makes matrix X similar to the sample tooth using a minimization task:

$$\min_{T_j} \sum_i (T_j(\bar{r}_i) - r_{ij})^2 = \min_{s_j, U_j, t_j} \sum_i (s_j U_j \bar{r}_t + t_j - r_{ij})^2,$$

where $\bar{r}_i$ is a vertex of the mean shape and $r_{ij}$ is a vertex of j-th sample tooth. The solution of the task for searching of the rigid transformation in closed form is well known and it may be freely generalized to a rigid+scale transformation.

Given transforms $T_j$, the matrix X may be redefined as:

$$X = \begin{pmatrix} r_{11} - T_1(\bar{r}_1) & r_{12} - T_2(\bar{r}_1) & \ldots & r_{1N} - T_N(\bar{r}_1) \\ r_{21} - T_1(\bar{r}_2) & r_{22} - T_2(\bar{r}_2) & \ldots & r_{2N} - T_N(\bar{r}_2) \\ \vdots & \vdots & \ddots & \vdots \\ r_{M1} - T_1(\bar{r}_M) & r_{M2} - T_2(\bar{r}_M) & \ldots & r_{MN} - T_N(\bar{r}_M) \end{pmatrix}$$

where each row contains vectors in cells and is treated as 3 ordinary rows.

Two viewpoints exist on how to limit the value of modes ($\alpha_1$). From a probabilistic viewpoint, the probability of x (ifs a vector collecting positions of all the mesh vertices) to be a tooth from normal distribution with the mean vector $\bar{e}$ and covariance matrix C is:

$$p \sim \exp[-\tfrac{1}{2}(x-\bar{e})^T C^{-1}(x-\bar{e})].$$

The expression may be used to filter out completely improbable teeth shapes. For example, a constant $c_1 \approx 10$ may be selected and only shapes satisfying the following equation are of interest:

$$(x-\bar{e})^T C^{-1}(x-\bar{e}) \leq c_1.$$

Taking the decomposition of $x-\bar{e}$ in basis formed from eigenvectors of matrix C:

$$x - \bar{e} = \sum_i \alpha_i v_i$$

and substituting it in the above equation yields:

$$\sum_i \frac{\alpha_i^2}{\lambda_i} \leq c_1. \quad (1)$$

In particular it gives:

$$\alpha_i \leq \sqrt{c_1 \lambda_i}.$$

Thus, if all the parameters $\alpha_i$ are within these limits, then the resulting linear combination of the corresponding eigenvectors and the mean tooth $$\left(\bar{e} + \sum_i \alpha_i v_i\right)$$

will give some probable shape of the tooth. Other values of $\alpha_i$ can be freely disregarded during tooth reconstruction.

From the Mesh degradation viewpoint, typically, the modes $\alpha_i$ are small corrections to the average shape. However, selecting $\alpha_i$ too large creates a large deviation from the average shape, which may cause the output shape to have large self-intersections, which are hard to resolve.

Thus, boundary values for parameters $\alpha_i$ are created to avoid undesirable self-intersections. Assuming the average shape does not include self-intersections, the following procedure is provided for detecting boundary values. The mode scales are limited to the values at which every face of the model changes its area and its normal, but not significantly relative to the face of average shape.

In this procedure, f is a face of the average shape E, and S(f, $\alpha$) is a vector with the direction of the normal to the face and magnitude equal to the area of the face for the given mode parameters $\alpha_i$. Since, translation and rotation parameters do not affect face area, S is a quadratic function of $\alpha$. Here, $S(f) = S(f, (1, 0, \ldots, 0))$ and boundary value $A_i$ is selected such that for any $|\alpha_i| \leq A_i$ the following equation holds:

$$\min_{f \in E} \frac{S(f)^T S(f, (1, 0, \ldots, \alpha_i, \ldots, 0))}{S^2(f)} \geq c$$

$$0 < c < 1.$$

Accordingly, this ensures that any face of the shape will not decrease its area lower than c-fraction of initial area while being affected by the change of the parameter $\alpha_i$ in the allowed range. This means, geometrically, that points of the face f are not too near to each other, which has been found to substantially lower the probability of self-intersections. To find $A_i$, a quadratic equation is solved for each models' face, then a global minimum may be found.

Referring again to FIG. 2, as a result of the analysis using PCA technique 204, the parametric model tooth mesh 206 is created. The parameters, may include, but are not limited to, number of cusps, cusp size, skew, height and width.

Once the tooth model mesh 206 has been created, tooth model mesh 206 (E(t, U, $\alpha$)) is fit to the original clinical crown mesh C which includes selecting parameters (t, U, $\alpha$) of tooth model mesh 206 in such a way that a certain "distance" between the model mesh 206 and clinical crown mesh C is minimal.

Figure 3:
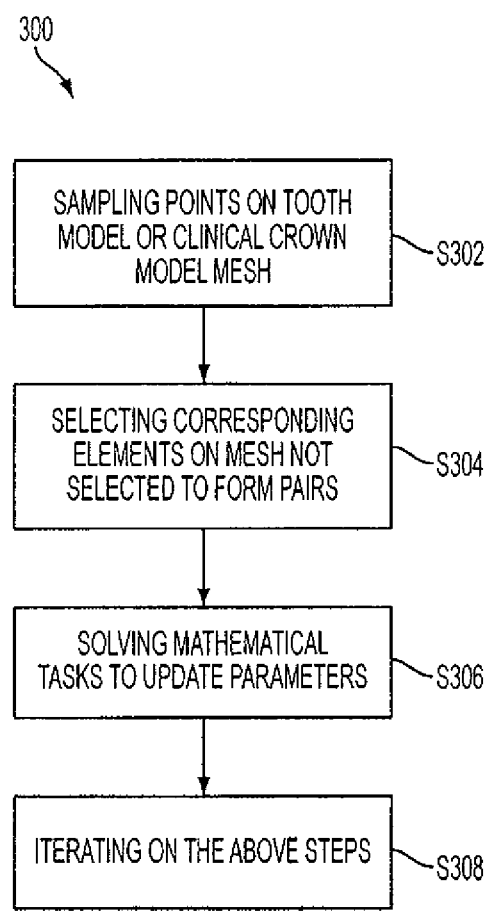
FIG. 3 is a flow diagram illustrating a computer-implemented process for fitting a tooth model to a clinical crown in accordance with an embodiment of the present invention.

As shown in FIG. 3, in one embodiment, process 300 of fitting tooth model mesh 206 to clinical crown mesh C includes the following stages: sampling (choosing) points on the surfaces of either tooth model mesh 206 or clinical crown mesh C (s302), selecting corresponding elements (points or faces) on the other mesh surface to form point pairs (s304), solving mathematical tasks which update the parameters bringing corresponding elements closer (minimizing the distance)(s306) and repeatedly iterating on the steps above (s308) to arrive at a coupling of the corresponding elements that minimizes the distance between the point pairs.

Figure 4:
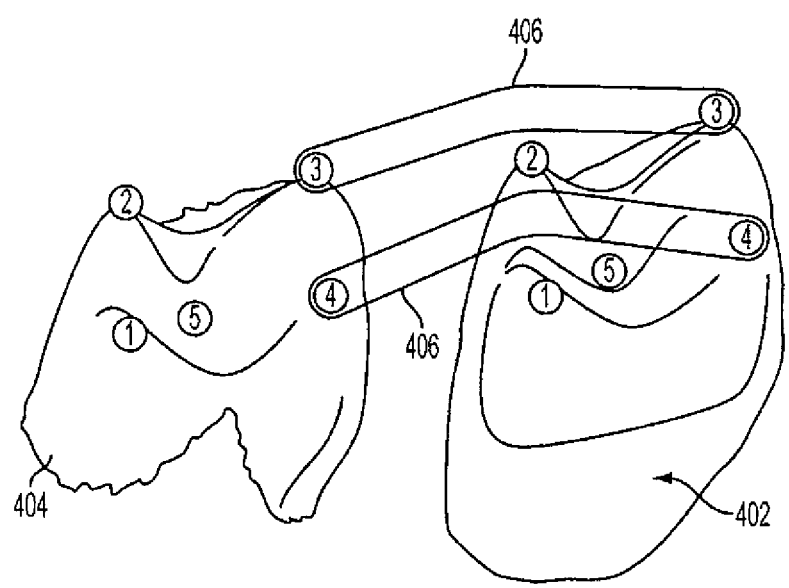
FIG. 4 is an illustration of corresponding point pairs on the tooth model and clinical crown in accordance with an embodiment of the present invention.

In step s302, as shown in FIG. 4, given tooth surface 402 of tooth model mesh 206 and clinical crown surface 404 from clinical crown mesh C, the surfaces 402 and 404 are "replaced" by approaching or converging sets of point pairs 406. Point pairs 406 may represent sufficiently details of surfaces 402 and 404. As described below, adequate coupling of point pairs 406 causes point pairs 406 to be located nearer relative to their present location in the iterative process when surfaces 402 and 404 are fitted together.

Although surfaces 402 and 404 may be processed simultaneously, in one embodiment, points are sampled on one of surfaces 402 or 404. In one embodiment, sampling proceeds by choosing distinguished points on the surfaces. For example, distinguished points may include the vertices of the triangular mesh thus created. In some embodiments, a weighting factor may be assigned to each point, such that the more weight assigned to a particular point the closer the point must approach the corresponding point on the other mesh. In one embodiment, for example, the weighting of a vertex may be made equal to the summed area of all faces incident to the vertex.

Introduction of point weighting alleviates problems that may arise due to nonuniformity of the mesh density—high and low densities of triangular elements. Thus, high density areas receive no advantage in matching over lower density areas.

The time of computation is dependent on the total number of points, thus to limit computation time, certain non-uniform vertices on the mesh may be eliminated. To simplify the mesh and bring the mesh density closer to uniformity, a decimation or simplification operation may be used to replace several vertices with one. One particular decimation method, such as collapsing of the shortest edge until its size is less than a threshold, provides fast and accurate performance.

Figure 5:
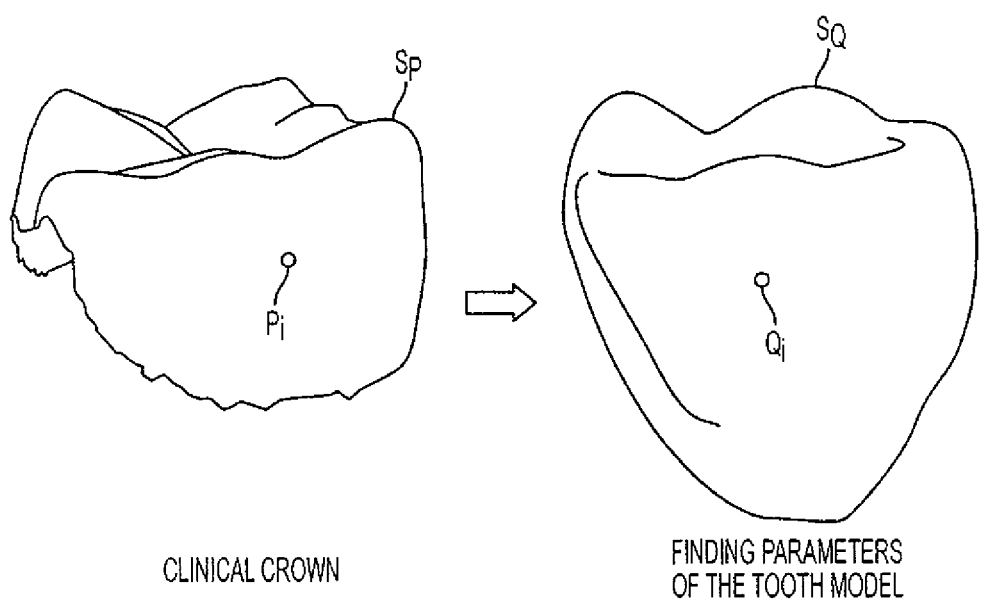
FIG. 5 is an illustration of surfaces of the tooth model and clinical crown in accordance with an embodiment of the present invention.

As a result of step s302, as shown in FIG. 5, a set of points $P_i$ from surface $S_P$ of either model tooth surface 404 or clinical crown surface 402 is created. In step s304, point pairs 306 $(P_i,Q_i)$ may be created by selecting appropriate points on surface $S_Q$.

In one embodiment, finding Q, involves taking the nearest point from the other surface:

$$Q = \text{proj}_{S_Q} P$$

Alternatively, finding Q involves taking the point of intersection of a line passing though point P with the direction given by the normal to $S_P$ at P.

$$Q \in S_Q \cap \text{line}(P, n_P).$$

Despite seeming different the ways have a similarity that the line connecting P and Q is orthogonal to either of surfaces (orthogonal to $S_P$ in the case of projection, orthogonal to $S_Q$ in the case of line intersection). Also in the case of line intersection P can be the nearest point to Q with sufficiently high probability: namely if P is located on the convex part of the surface (if viewing from Q).

In the process 300 of fitting the tooth model to the clinical crown, it may happen that certain regions (root, interproximal area) on the tooth model may have no corresponding regions on the clinical crown, which creates an error that affects the fitting if some pairs are formed for that region. If the clinical crown surface is initially chosen for point sampling (s302) then these regions are ignored automatically. Otherwise, if points are sampled on the tooth model, explicit filtering of the pairs may be needed.

Figure 6:
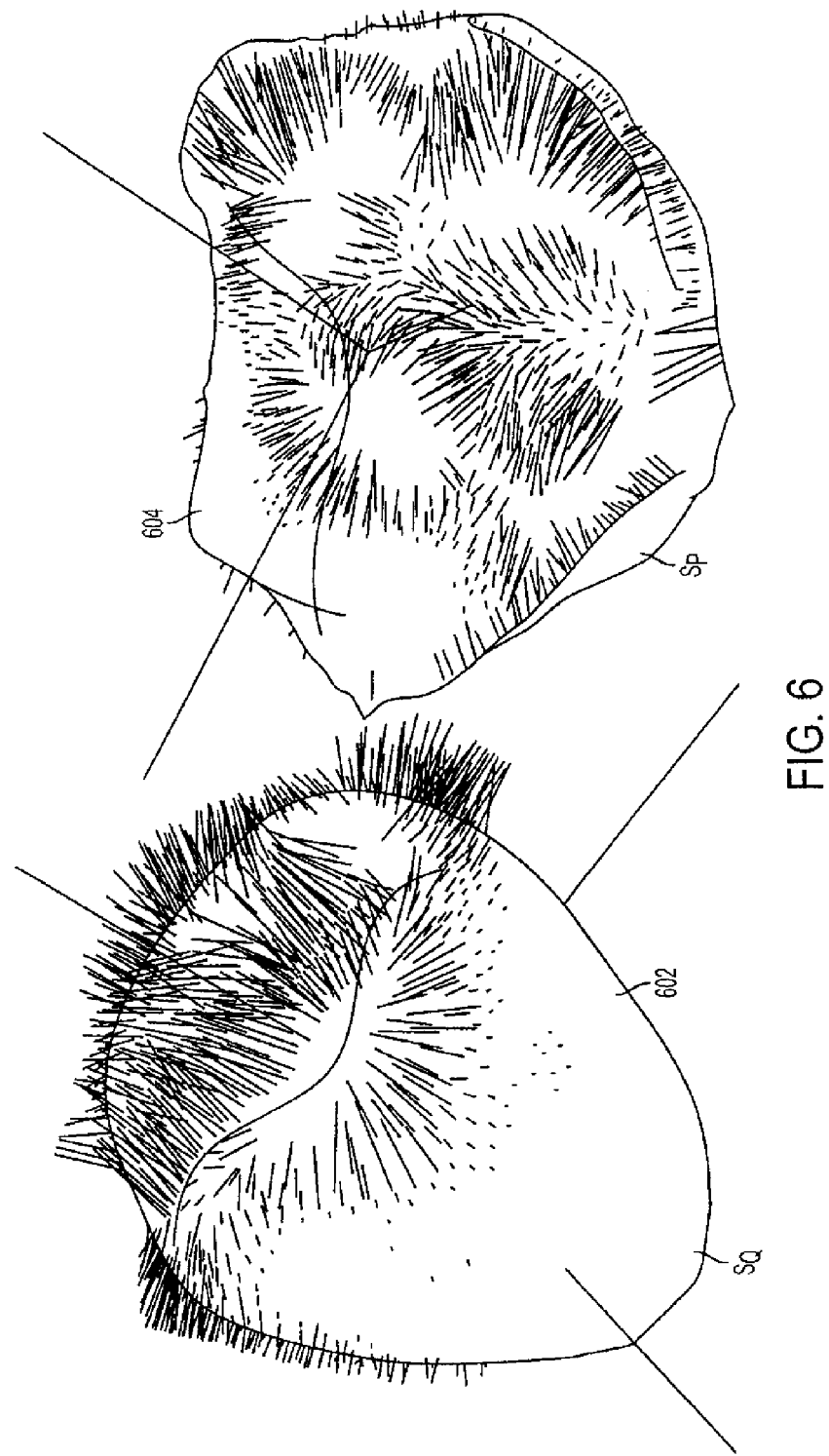
FIG. 6 is an illustration of pairs formed using projections in accordance with an embodiment of the present invention.

FIG. 6 is an illustration of an embodiment, in which tooth model 602 is sampled and projections are found on clinical crown 604. The filtering of point pairs may be governed by the following: 1) If P is projected on the boundary of the clinical crown 604, the pair is rejected; 2) considering the vector $d=(-1)^s(P-Q)$, with its direction chosen so that the scalar product of d and the normal to $S_Q$ at Q is a positive value, if the angle between d and the normal to P at $S_P$ is larger than a certain threshold, for example, 60°, the pair is discarded; and 3) considering the distance $\|d\|$ between the points of a pair in comparison with the root-mean-square distance $\bar{d}$ of all the pairs before filtering, if $\|d\|>\sigma_0\bar{d}$, the pair is rejected (3-sigma rule). The filtering process allows precise "projectors" and "intersectors" to be replaced with faster approximation methods.

After each point on one mesh surface receives a corresponding point on the other mesh surface, transformations are made that match the points of each pair together according to their weights. In one embodiment, point-to-point matching is used. In this embodiment, a set of pairs may be denoted as $(P_i,Q_i)$, the weight as $w_i$, and the parameterized transformation as T. The functional below is minimized:

$$\min_T \sum_i w_i \|P_i - T(Q_i)\|^2. \qquad (2)$$

However, recall that the points are not isolated but represent meshes and several iterations may have to be done in order to achieve the best fitting. Accordingly, the same sample points may probably be chosen on subsequent iterations and correspondences are received by projecting them on the other mesh. If the transformation found on the current iteration is small enough which is a typical case in the iteration process, then the projections of the sample points with high probability fall on the same faces as on the current iteration, or may be on the neighboring faces which have similar directions of normals. To facilitate the process, a point-to-plane transformation may be used where each face may be extended to the plane containing it to find the transformation minimizing distances of the sample points to these planes. In principle, point-to-planes matching increases the speed of convergence process because each iteration of point-to-planes matching is roughly equivalent to several iterations of point-to-point matching. Consequently, much lesser number of timely projections on a mesh must be computed. For this reason, in some embodiments, point-to-point matching may be used alone or in conjunction with point-to-planes matching.

In steps s306, after pairs of corresponding points on the surfaces of tooth model 602 and clinical crown 604 are formed, the transformation is performed that brings the two surface meshes 602 and 604 together. The 3D transformations that may be used include:

Translation $$P=T_t(Q)=Q+t \qquad (4)$$

Rigid-body transformation $$P=T_{U,t}(Q)=UQ+t, UU^T=I. \qquad (5)$$

Rigid-body transformation with scaling $$P=T_{U,t}(Q)=sUQ+t, UU^T=I. \qquad (6)$$

Reflection relative to a line $$P=T_{t,n}(Q)=2(t+(Q^Tn)n)-Q, n^2=1, t-(t^Tn)n=0, \qquad (7)$$

where n is a unit directional vector of the line, t-point on the line nearest to the origin.

Reflection relative to a plane $$P=T_{d,n}(Q)=Q+2(d-Q^Tn)n, n^2=1, \qquad (8)$$

where n is a unit normal to the plane, d-signed distance from the plane to the origin.

Given pairs $\{P_i,Q_i\}$ the constrained least-squares problem equation (2) may be solved for any of the transformation groups.

Not only rigid transformation of the tooth model may be found with the generalization of equation (2), but also modes parameters α. The concern at this point in process 300 is no longer 3D transformations, but with mapping from 3A-dimensional space to 3-dimensional space, where A is the number of modes.

Figure 7:
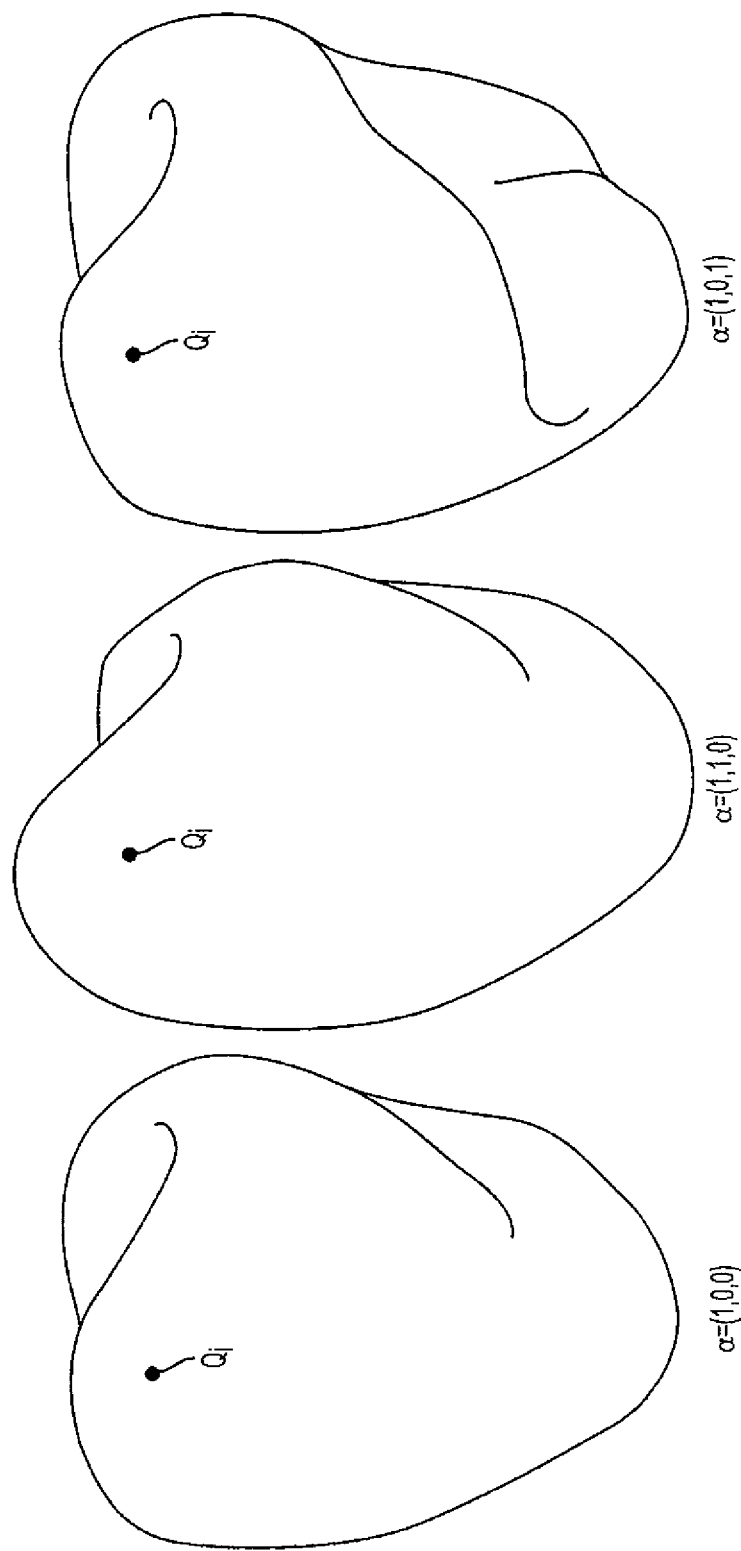
FIG. 7 is an illustration of mode fitting in accordance with an embodiment of the present invention.

In this example, as shown in FIG. 7, every mode may be considered a triangular mesh, each sharing the same topology. Thus, the model tooth is a linear combination of the mode meshes. Given point Q on the model tooth, the corresponding points of the mode meshes may be restored using the index of the triangle to which Q belongs. All points may be collected in 3×A matrix Q, then Q=Qα.

Thus the functional to be minimized takes the form:

$$\min_{T,\alpha} \sum_i w_i \|P_i - T(Q_i)\alpha\|^2.$$

Here, T belongs to the class of rigid-body transformations (5). The functional may be rewritten using the property of orthogonal matrices: $x^2 = (U^T x)^2$:

$$\min_{U,t,\alpha} \sum_i w_i \|Q_i\alpha + U^T t - U^T P_i\|^2.$$

The minimum may be found using some simplifications. The rotation around the axis, given by a unit vector r, on the angle φ can be represented as:

$$U^T P = (rr^T)P + \cos\phi (I - rr^T)P + \sin\phi [P, r].$$

Thus, it is expected that the mapping changes are not significant and becomes less and less significant if convergence takes place, particularly the rotation. In the approximation of small angles: $\sin\phi \approx \phi$, $\cos\phi \approx 1$, action of the rotation matrix may be represented as:

$$U^T P \approx P + \varphi[P, r] = P + [P, \alpha] = P + \Omega(P)\alpha,$$

$$a = \varphi r, \Omega(P) = \begin{bmatrix} 0 & -P_z & P_y \\ P_z & 0 & -P_x \\ -P_y & P_x & 0 \end{bmatrix}$$

Substituting $U^T P$ back into the functional, yields:

$$\min_{U,a,t,\alpha} \sum_i w_i \|Q_i\alpha + U^T t - P_i - \Omega(P_i)a\|^2.$$

Collecting all the variables in one vector x={α,α}, and the coefficients in one matrix:

$$Q'_i[Q_i \Omega^T(P_i) \in R^{3 \times (A+3)}.$$

Thus, the simplified view of the functionals:

$$\min_{x,t} \sum_{i=1}^n w_i \|Q'_i x + U^T t - P_i\|^2.$$

In one embodiment, it may be desired to set tooth orientation manually. Then T is taken from the class of translations (4). In that embodiment, the above form is valid if U=1, x=α, Q'=Q. For the sake of brevity, the stroke next to Q is omitted.

Setting the derivative on $U^T t$ to zero, yields:

$$t = U(\langle P \rangle - \langle Q \rangle x),$$

where:

$$\langle P \rangle = W^{-1} \sum_{i=1}^n w_i P_i, \langle Q \rangle = W^{-1} \sum_{i=1}^n w_i Q_i, W = \sum_{i=1}^n w_i.$$

Transforming over to a central coordinate system yields:

$$p_i = P_i - \langle P \rangle, q_i = Q_i - \langle Q \rangle,$$

then, the optimization task is simplified:

$$\min_x \sum_{i=1}^n w_i (q_i x - p_i)^2 = \min_x (x^T A x + 2 b^T x + f),$$

$$A = \sum_{i=1}^n w_i Q_i^T Q_i - W^{-1} \langle Q \rangle^T \langle Q \rangle, b = \sum w_i Q_i^T P_i - W^{-1} \langle Q \rangle^T \langle P \rangle.$$

Note, that the last three values of b is zero due to equation $\Omega(p_i)p_i = 0$.

Using the equations above reduces the task of modes fitting to the minimum finding of a multivariate quadratic function. However, since the variables are not independent, they must satisfy the inequation (1). This inequation limits the modes parameters implying that they are added to the average tooth. During the fitting, the model tooth is allowed to scale entirely and the average tooth is considered as one of the modes with scale coefficient, thus (1) is generalized to:

$$\sum_{i=2}^A \frac{\alpha_i^2}{\lambda_i} \le c_1 \alpha_1^2.$$

Figure 8:
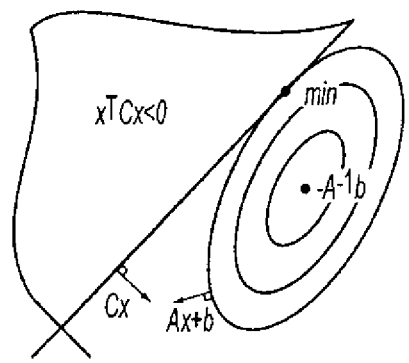
FIG. 8 is a schematic illustration of a solution to an algorithmic problem in accordance with an embodiment of the present invention.

As noted in FIG. 8, an observation about the inequation above is that it includes only squares of the variables. Thus, the mathematical problem may be stated as follows:

$$\min_{\vec{x}^T c \vec{x} \le 0} (\vec{x}^T A \vec{x} + 2 \vec{b}^T \vec{x}) \quad (10)$$

where A—symmetric positive defined matrix n×n, C—diagonal matrix of the same size having values of different signs. More precisely C has only one negative element.

As a first step, the minimum of unconstrained problem $\vec{x} = -A^{-1}\vec{b}$ is taken. If it satisfies the condition $\vec{x}^T C \vec{x} \le 0$, then the solution is found. Otherwise, find the minimum of $$\min_{\vec{x}^T c \vec{x} = 0} (\vec{x} A \vec{x} + 2 \vec{b}^T \vec{x}), \quad (11)$$

The problem may be solved using a Lagrange multipliers method. Setting derivatives equal to zero produces the system of equations:

$$A\vec{x}+\vec{b}-\mu C\vec{x}=0,$$

$$\vec{x}^T C\vec{x}=0. \quad (12)$$

Then multiply the first row on $\vec{x}$ and take into account the second row:

$$\vec{x}^T A\vec{x}+\vec{b}^T\vec{x}=0.$$

Substituting back in (11), from all the solutions $(\vec{x},\mu)$ it is required to choose one that gives minimum to $\vec{b}^T\vec{x}$.

Making use of Holesky decomposition: $A=LL^T$, and changing the variables $\vec{y}=L^T\vec{x}$ in (12), denote $D=L^{-1}C(L^T)^{-1}$, $\vec{e}=L^{-1}\vec{b}$ as a result:

$$\vec{y}+\vec{e}-\mu D\vec{y}=0,$$

$$\vec{y}^T D\vec{y}=0. \quad (13)$$

By construction the matrix D is also symmetric, and includes a full set of orthogonal eigenvectors $\{\vec{\omega}_i\}$, which are placed in the columns of $\Omega$:

$$D\Omega=\Omega\Lambda, \Omega\Omega^T=I, \Lambda=\text{diag}(\lambda_i).$$

Substitute in (13) $\vec{z}$ for $\Omega^T\vec{y}$:

$$\vec{z}-\mu\Lambda\vec{z}=-\vec{g}, (\vec{g}=\Omega^T\vec{e})$$

$$\vec{z}^T\Lambda\vec{z}=0. \quad (14)$$

Knowing that $-A^{-1}\vec{b}$ does not satisfy the condition $\vec{x}^T C\vec{x}\geq 0$, thus $$\vec{b}^T A^{-1}CA^{-1}\vec{b}>0, \Leftrightarrow \vec{e}^T D\vec{e}>0, \Leftrightarrow \vec{g}^T\Lambda\vec{g}>0.$$

Substitution of the first row of (14) in the second gives $$0=\vec{g}^T(\mu\Lambda-I)^{-1}\Lambda(\mu\Lambda-I)^{-1}\vec{g}=\sum_i\frac{\vec{g}_i^2\lambda_i}{(\mu\lambda_i-1)^2}$$

Consider the function $$f(\mu)=\sum_i\frac{\vec{g}_i^2\lambda_i}{(\mu\lambda_i-1)^2},$$

that has the solution among its roots. The interest is in the points where the gradient of $\vec{x}^T A\vec{x}+2\vec{b}^T\vec{x}$ is directed oppositely to the gradient of $\vec{x}^T C\vec{x}$, that is $\mu<0$, because if not, the source quadratic function is lesser inside the cone: $\vec{x}^T C\vec{x}<0$.

Until now, the property that C has only one negative element, has not been used. It follows from the condition $\vec{g}^T\Lambda\vec{g}>0$ that $f(0)>0$. The application of Sylvester's law of inertia to D allows that among $\lambda_i$ there is exactly one negative eigenvalue $\lambda_-$. Therefore:

$$\lim_{\mu\to\lambda_-^{-1}}f(\mu)\to-\infty.$$

Because of one negative root $\mu$ always exists in the range $(\lambda_-^{-1},0)$. And if $\vec{g}^T\Lambda^{-1}\vec{g}>0$, then there is the second negative root in the range $(-\infty, \lambda_-^{-1})$. The method of numerical root finding on these intervals is used to obtain the solution.

As soon as a new approximation of matching transformations is obtained, it is possible to form other pairs of points and repeat the process. However, another approach may be seen from a performance perspective. It is possible to leave one of the point sets intact and update only the other. In the case of saving Q, $P^{n+1}$ is obtained as the projections of Q on the surface $S_Q$. In the other case (P is unchanged), it is best to search $Q^{n+1}=\text{proj}_{S_Q}T^{-1}(P)$. Thus, there is no need to update search structures for $S_Q$ on every iteration.

Figure 9:
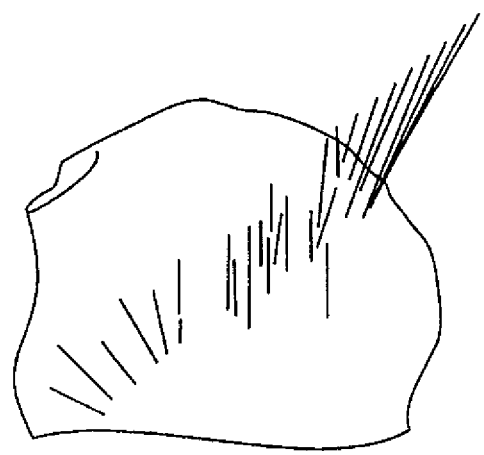
FIG. 9 is a simplified demonstration of an approximated projection on a surface of a point moving along a line from bottom-left in accordance with an embodiment of the present invention.

In one embodiment referring to FIG. 9, to accelerate the process, note that a replaced value of a point (let it be $P^n$) is a good initial approximation for the projection $P^{n+1}$, especially on the later iterations when the change in transformation is not significant. Instead of finding true projection of T(Q), find the nearest point to T(Q) on the face, containing $P_n$. If the point is not on the boundary of the face, take it as $P^{n+1}$. Otherwise inspect incident faces to that boundary point. During the inspection the nearest known point on $S_P$ to T(Q) is kept. The inspection stops as soon as the distance to projection approximation stops diminishing. In the case of convex surface $S_P$ from the point T(Q), the process converges to the nearest point. In the worst case when $P^{n+1}=P^n$, on the next iteration an attempt is made to bring together the same pairs of points, thus decreasing the convergence, but it in no way spoiling the currently known approximation of the transformation.

Practical experiments have shown that the best strategy is to interleave slow steps where pairs are fully updated (several such steps in series at the beginning and rarely later) with the fast steps when pairs are updated approximately and partially. Doing so makes it possible to achieve the same quality, as if repeating only slow steps, but on an order of magnitude faster.

To control convergence of the iterations, the value of the functional (2) must be watched. Unfortunately, control depends on the pairs selected and may occasionally rise if pairs of points are rebuilt completely. To overcome this, tight bounding box $B_Q$ may be built around surface $S_Q$ and watched at the corners. It may be shown that given two transformations $T_{1,2}$ from one of the groups above:

$$\max_{p\in S_Q}|T_1(p)-T_2(p)|$$

is not greater than the shift $T_1-T_2$ of one of the corners of the bounding box. So watching the maximum shift of the corners may give a cue when to stop iterations.

Since the pairs selection depends on the model parameters, pairs matching may be used to the iterative procedure of consequent pairs selection and model update. An example of a pseudo code for minimization procedure may take the form:

```
int iter = 0
Pairs pairs;
Model model;
```

-continued

```
// this initialize model with the zero order approximation
model.initialize( );
do
    // use model with given parameters to reconstruct pairs
    formPairs (model, pairs);
    // use pairs to modify model parameters to minimize F
    matchPairs (model, pairs);
while (iter < maxIter);
```

Initial state of the model is deduced from the manual input.

Figure 10:
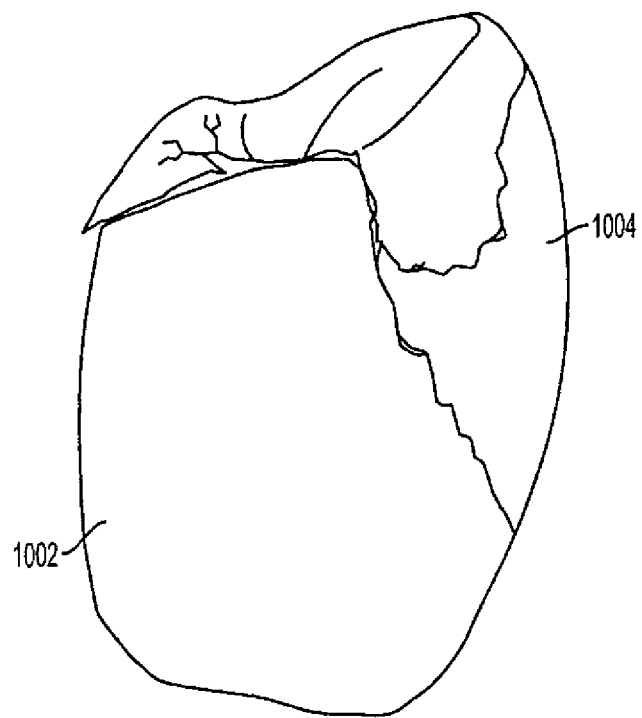
FIG. 10 is a representation of a resulting matched model and the original crown to which it is intended to match in accordance with an embodiment of the present invention.

Once the matching procedure is complete, the result is a matched model 1002 and original crown 1004 as represented in FIG. 10. These surfaces are similar, but not yet the same. Thus, matched model 1002 may be morphed to original crown 1004 to more closely approximate the surface of original crown 1004 and keep the shape anatomical at the same time.

For teeth having a typical anatomy, the shape modification during the morphing stage may be relatively small. However, exceptional cases may exist having unusual tooth anatomy not represented by the set of etalon teeth set (FIG. 2). Unusual anatomy may occur, for example, if a tooth was physically damaged and/or unusually worn.

Figure 11:
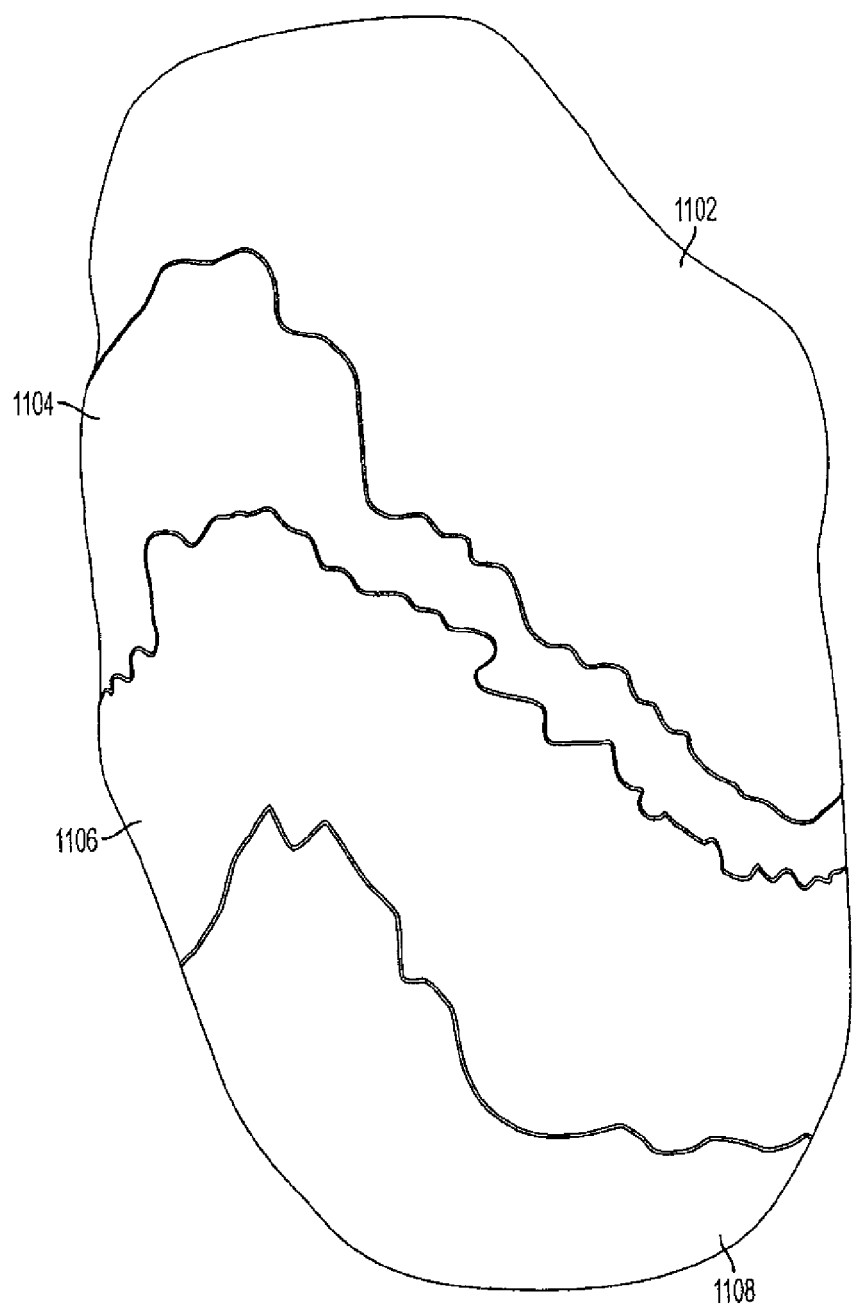
FIG. 11 is a simplified illustration of a clinical crown divided into four regions as used in accordance with an embodiment of the present invention.

Morphed shape 1006 satisfies the following criteria, in various combinations: it is smooth; it follows original crown 1004; it mimics matched model 1002 in the rest places; and it is more convex than concave. The proper combination of criteria depends on the point location. Thus, to achieve this, as shown in FIG. 11, the whole tooth surface is divided into 4 regions: 1) inner crown 1102; 2) crown boundary 1104; 3) reconstructed shape boundary 1106; and 4) reconstructed root 1108.

The segmentation is based on the projection of matched model 1002 to original crown 1004. Assuming that the vertex v of matched model 1002 belongs to original crown 1004 if u=proj$_C$(v) does not belong to the boundary of C, and either:

$$\angle(n_v, u-v) \leq \alpha_0,$$

or a ray $R(v, \pm n_v)$ intersects original crown 1004 at some point w and $$\angle(n_v, n_w) \leq \alpha_0.$$

This allows for a distinguishment of vertices from regions 1 and 2 (crown vertices) and vertices from regions 3 and 4 (reconstructed and root vertices).

To distinguish regions 1 and 2 a predefined size of the boundary region is used. Thus, the vertex v belongs to the region 2 if the distance (in edges) from v to the boundary of original crown 1004 part of the model is less than a certain threshold distance. A similar rule is applicable to distinguishing regions 3 and 4.

Smoothing is governed by rules that describe transformation of a single vertex. The processing of a vertex depends on the region to which it belongs (FIG. 11). Thus, for example:
1. Reconstructed root 1108. Do nothing:

$$p_i^{n+1} = p_i^n.$$

2. Inner crown 1102:

$$p_i^{n+1} = \alpha <p_i^n> + (1-\alpha) c^{proj}(<p_i^n>).$$

where $<p_i^n>$ defines the averaged position of $p_i^n$ and neighbor vertices. α—constant parameter required to assure stability of the iteration process.

3. Reconstructed shape boundary 1106:

$$p_i^{1+1} = \alpha <p_i^n> + (1-\alpha) h_i n_i^n,$$

where $n_i$—normal at the vertex, $h_i$ is the 'height' of the vertex computed on the model shape in the zero iteration:

$$h_i = (p_i^0 - <p_i^0>) n_i^0.$$

It's probably the simplest measure of curvature of the etalon shape. Addition of the height required to compensate shrinkage due to ordinary Laplacian smoothing, which is defined by the transformation $p^{n+1} = <p^n>$ 4. Crown boundary 1108

In this region the rules of processing are intermediate between inner crown 1102 and reconstructed shape boundary region 1106 with the coefficient linearly dependent on the distance. Thus, there is smooth transition in processing between the three regions.

Figure 12:
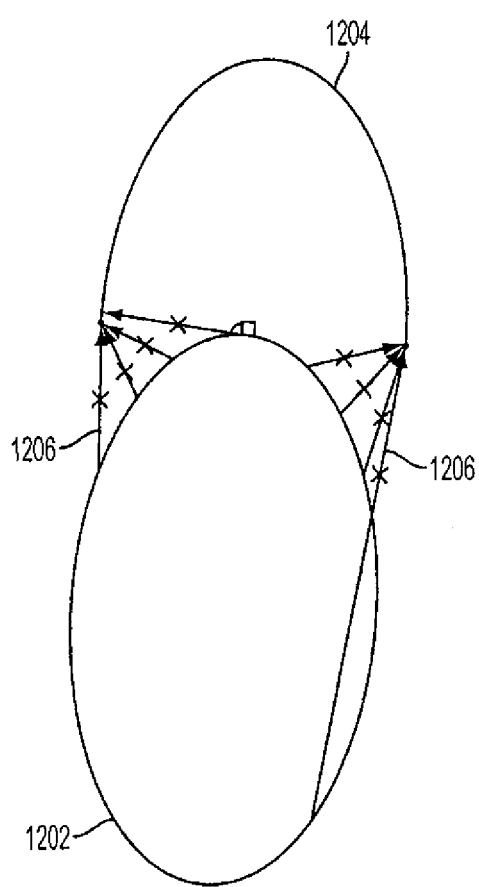
FIG. 12 is a simplified illustration of a complexity associated with morphing of a matched model with a clinical crown near an area of significant convexity in accordance with the present invention.

It has been found that divergence of matched model 1002 and original crown 1004 may be high, especially in areas with high crown curvature and bad initial matching, even if all the tooth vertices are located on the crown. As shown in FIG. 12, morphing of a tooth 1202 near an area of significant crown convexity 1204, using projection to the nearest point, shown by arrows 1206, leads to significant divergence between surfaces.

To alleviate the problems, movement along a line may not be farther than a distance to the projection point. This diminishes leaps of vertices as soon as they approach a crown. Also, direction of normals are not recomputed during the first half of iterations, while the surfaces are not near enough.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, for example, various of the component and methodologies and/or steps may be deleted, modified, or combined with other components, methodologies and/or steps. These and other functions, methods, changes or modifications are intended to be included within the scope of the present invention, as set forth in the following claims.

What is claimed is:

1. A computer-implemented method for modeling a complete tooth of a patient to facilitate dental and/or orthodontic treatment comprising:

generating a first set of digital data representing a clinical crown;

generating a second set of digital data representing a plurality of digital tooth models of a particular tooth type each having a first parameterization;

processing the second set of digital data to obtain a third set of digital data representing an average tooth model of the particular tooth type having a second parameterization which is less than the first parameterization and representing surfaces of the average tooth model with a mesh;

fitting the third set of digital data to the first set of digital data to create a set of digital data representing an interim tooth model, wherein fitting the third set of digital data to the first set of digital data comprises:

a) sampling points on a surface represented in one of the first set or the third set of digital data;

b) forming point pairs, each point pair including a respective sampled point in the one of the first set or the third set of digital data and a corresponding point in an other of the first set or the third set of digital data, by projecting the sampled points from the one of the first set or the third set of digital data to an other of the third set or the first set of digital data;

c) transforming the point pairs to bring the first set and the third set of digital data together; and repeating steps a), b), and c), wherein a subsequent repetition of steps a), b), and c) includes sampling a same sampled point from a previous iteration, using one of the transformed point pairs as an initial approximation for a projection of the same sampled point, and finding a nearest point on a face containing the one of the transformed point pairs rather than finding a true projection of the same sampled point; and morphing the set of digital data representing the interim tooth model to substantially mimic the anatomical shape of the clinical crown of the first set of digital data.

2. The computer-implemented method of claim 1, further comprising assigning a weighting factor to each point of the mesh, wherein transforming the point pairs comprises transforming the point pairs to cause the points to converge based on their assigned weighting factor.

3. The computer-implemented method of claim 2, wherein assigning the weighting factor comprises assigning a weighting factor to respective vertices in the mesh equal to a summed area of those faces of the mesh incident to the respective vertex.

4. The computer-implemented method of claim 1, further including filtering the point pairs such that:

rejecting a point pair in response to a point being projected on a boundary of the first set of digital data;

rejecting a point pair in response to an angle between a normal to the clinical crown at a projected point and a vector between the point and the projected point being beyond a threshold; and rejecting a point pair in response to a distance between the point pair being greater than three sigma from the root-mean-square distance of all the point pairs before filtering.

5. The computer-implemented method of claim 1, wherein repeating steps a), b), and c) includes leaving either the sampled points or the points paired with the sampled points intact and updating other points.

6. The computer-implemented method of claim 1, wherein finding the nearest point on the face containing the one of the transformed point pairs includes using the nearest point as a next value of the sampled point if it is not on a boundary of the face.

7. The computer-implemented method of claim 6, wherein using the one of the transformed point pairs as the initial approximation for the projection includes inspecting incident faces to the boundary if the nearest point to the one of the transformed point pairs is on the boundary and using a point on one of the incident faces as the next value of the same sampled point.

8. The computer-implemented method of claim 1, wherein transforming the point pairs comprises using point-to-planes matching and using point-to-point matching.

9. The computer-implemented method of claim 1, wherein morphing the set of digital data representing the interim tooth model includes dividing a tooth surface of the interim tooth model into regions including an inner crown, a crown boundary, a reconstructed shape boundary, and a reconstructed root.

10. The computer-implemented method of claim 9, wherein morphing the set of digital data representing the interim tooth model includes distinguishing vertices in the inner crown region and the crown boundary region from vertices in the reconstructed shape boundary region and the reconstructed root region.

11. The computer-implemented method of claim 10, wherein morphing the set of digital data representing the interim tooth model includes:

distinguishing the vertices in the inner crown region from the vertices in the crown boundary region; and distinguishing the vertices in the reconstructed shape boundary region from the vertices in the reconstructed root region.

12. The computer-implemented method of claim 9, wherein morphing the set of digital data representing the interim tooth model includes smoothing a shape of the interim tooth model by:

doing nothing for vertices in the reconstructed root region;

transforming a vertex in the inner crown region according to the equation:

$$p_i^{n+1} = \alpha \langle p_i^n \rangle + (1-\alpha)\text{proj}_C(\langle p_i^n \rangle)$$

where $p_i$ is a position of a vertex in the inner crown region, $\langle p_i^n \rangle$ is an averaged position of $p_i^n$ and neighboring vertices, $\alpha$ is a stability constant, and C is a mesh representing the crown.

13. The computer-implemented method of claim 9, wherein morphing the set of digital data representing the interim tooth model includes smoothing a shape of the interim tooth model by transforming a vertex in the reconstructed shape boundary region according to the equation:

$$p_i^{n+1} = \alpha \langle p_i^n \rangle + (1-\alpha)h_i n_i^n$$

where $p_i$ is a position of a vertex in the inner crown region, $\langle p_i^n \rangle$ is an averaged position of $p_i^n$ and neighboring vertices, $\alpha$ is a stability constant, h is a height of the vertex computed on the shape of the interim tooth model in a zeroth iteration, and n is a normal at the vertex.

14. The computer-implemented method of claim 9, wherein morphing the set of digital data representing the interim tooth model includes smoothing a shape of the interim tooth model by transforming a vertex in the crown boundary region intermediately between the equations:

$$p_i^{n+1} = \alpha \langle p_i^n \rangle + (1-\alpha)\text{proj}_C(\langle p_i^n \rangle); \text{ and}$$

$$p_i^{n+1} = \alpha \langle p_i^n \rangle + (1-\alpha)h_i n_i^n$$

$$p_i^{n+1} = \alpha \langle p_i^n \rangle + (1-\alpha)h_i n_i^n$$

where $p_i$ is a position of a vertex in the inner crown region, $\langle p_i^n \rangle$ is an averaged position of $p_i^n$ and neighboring vertices, $\alpha$ is a stability constant that is linearly dependent on distance, h is a height of the vertex computed on the shape of the interim tooth model in a zeroth iteration, n is a normal at the vertex, and C is a mesh representing the crown.

15. A computer-implemented method for modeling a complete tooth of a patient to facilitate dental and/or orthodontic treatment comprising:

generating a first set of digital data representing a clinical crown;

generating a second set of digital data representing a plurality of digital tooth models of a particular tooth type each having a first parameterization;

processing the second set of digital data to obtain a third set of digital data representing an average tooth model of the particular tooth type having a second parameterization which is less than the first parameterization and representing surfaces of the average tooth model with a mesh;

fitting the third set of digital data to the first set of digital data to create a set of digital data representing an interim tooth model; and morphing the set of digital data representing the interim tooth model to substantially mimic the anatomical shape of the clinical crown of the first set of digital data including dividing a tooth surface of the interim tooth model into regions including an inner crown, a crown boundary, a reconstructed shape boundary, and a reconstructed root, wherein the inner crown region is distinguished from the crown boundary region based on a predefined size of the crown boundary region such that a vertex in either the inner crown region or the crown boundary region belongs to the crown boundary region rather than the inner crown region if a distance, determined by a number of edges of the mesh, from the vertex to a boundary of the original clinical crown in the first set of digital data is less than a threshold distance, wherein the boundary of the original clinical crown is a boundary between the original clinical crown and the reconstructed shape boundary.

16. The computer-implemented method of claim 15, wherein morphing the set of digital data representing the interim tooth model includes smoothing a shape of the interim tooth model by:

doing nothing for vertices in the reconstructed root region;

transforming a vertex in the inner crown region according to the equation:

$$p_i^{n+1} = \alpha \langle p_i^n \rangle + (1-\alpha)\mathrm{proj}_C(\langle p_i^n \rangle)$$

transforming a vertex in the reconstructed shape boundary region according to the equation:

$$p_i^{n+1} = \alpha \langle p_i^n \rangle + (1-\alpha) h_i n_i^n$$

transforming a vertex in the crown boundary region intermediately between the equations:

$$p_i^{n+1} = \alpha \langle p_i^n \rangle + (1-\alpha)\mathrm{proj}_C(\langle p_i^n \rangle); \text{ and}$$

$$p_i^{n+1} = \alpha \langle p_i^n \rangle + (1-\alpha) h_i n_i^n$$

where $p_i$ is a position of a vertex in the inner crown region, $\langle p_i^n \rangle$ is an averaged position of $p_i^n$ and neighboring vertices, $\alpha$ is a stability constant that is linearly dependent on distance, h is a height of the vertex computed on the shape of the interim tooth model in a zeroth iteration, n is a normal at the vertex, and C is a mesh representing the crown.

17. The computer-implemented method of claim 15, wherein fitting the third set of digital data to the first set of digital data comprises:

a) sampling points on a surface represented in one of the sets of digital data;

b) forming point pairs using corresponding points on the surface represented in another one of the sets of digital data;

c) transforming the point pairs to cause the points of each point pair to converge; and repeating steps a), b), and c) to couple the point pairs.

18. A computerized system for modeling a complete tooth crown of a patient to facilitate dental and/or orthodontic treatment, said computerized modeling system comprising:

a microprocessor; and a memory device, said microprocessor configured to:

generate a first set of digital data representing a clinical crown;

generate a second set of digital data representing a plurality of digital tooth models of a particular tooth type each having a first parameterization;

process the second set of digital data to obtain a third set of digital data representing an average tooth model of the particular tooth type having a second parameterization which is less than the first parameterization and representing surfaces of the average tooth model with a mesh;

assign a weighting factor to each point of the mesh equal to a summed area of those faces of the mesh incident to each point;

fit the third set of digital data to the first set of digital data to create a set of digital data representing an interim tooth model, wherein fitting the third set of digital data to the first set of digital data comprises:

a) sampling points on a surface represented in one of the first set or the third set of digital data;

b) forming point pairs, each point pair including a respective sampled point in the one of the first set or the third set of digital data and a corresponding point in an other of the first set or the third set of digital data, by projecting the sampled points from the one of the first set or the third set of digital data to an other of the third set or the first set of digital data;

c) transforming the point pairs to bring the first set and the third set of digital data together based on an assigned weighting factor of the point pairs; and repeating steps a), b), and c) to couple the point pairs; and morph the set of digital data representing the interim tooth model to substantially mimic the anatomical shape of the clinical crown of the first set of digital data including dividing a tooth surface of the interim tooth model into regions including an inner crown, a crown boundary, a reconstructed shape boundary, and a reconstructed root.

19. The system of claim 18, wherein said microprocessor is configured, on a subsequent repetition of steps a), b), and c), to use a transformed point pair in the other of the first set or the third set of digital data as an initial approximation for a projection of a corresponding point from the one of the first set or the third set of digital data rather than finding the projection of the corresponding point.

20. The system of claim 19, wherein said microprocessor being configured to use the transformed point pair as the initial approximation for the projection includes said microprocessor being configured to find a nearest point to the transformed point pair on a face containing the sampled point and use it as a next value of the sampled point if it is not on a boundary of the face.

* * * * *